(12) United States Patent
Bostrom et al.

(10) Patent No.: US 7,384,453 B2
(45) Date of Patent: Jun. 10, 2008

(54) SELF-CONTAINED CHROMATOGRAPHY SYSTEM

(75) Inventors: Neil W. Bostrom, Norwalk, CT (US); Robert L. Kleinberg, Ridgefield, CT (US)

(73) Assignee: Schlumberger Technology Corporation, Ridgefield, CT (US)

(*) Notice: Subject to any disclaimer, the term of this patent is extended or adjusted under 35 U.S.C. 154(b) by 211 days.

(21) Appl. No.: 11/296,150

(22) Filed: Dec. 7, 2005

(65) Prior Publication Data

US 2007/0125233 A1    Jun. 7, 2007

(51) Int. Cl.
*B01D 53/02* (2006.01)

(52) U.S. Cl. .............................. 95/82; 96/101; 96/105; 96/106; 73/23.42

(58) Field of Classification Search .............. 95/82; 96/101, 102, 105, 106; 73/23.35, 23.37, 73/23.38, 23.42; 210/198.2, 656
See application file for complete search history.

(56) References Cited

U.S. PATENT DOCUMENTS

| | | | | |
|---|---|---|---|---|
| 3,537,585 A | * | 11/1970 | Waters | 210/198.2 |
| 3,581,465 A | * | 6/1971 | Haruki et al. | 95/87 |
| 3,589,171 A | | 6/1971 | Haley | |
| 3,638,396 A | * | 2/1972 | Lovelock | 95/56 |
| 4,739,654 A | | 4/1988 | Pilkington et al. | 73/155 |
| 4,935,040 A | | 6/1990 | Goedert | |
| 4,960,444 A | * | 10/1990 | Ghaoui | 95/88 |
| 4,994,096 A | * | 2/1991 | Klein et al. | 95/15 |
| 5,305,775 A | | 4/1994 | Farwell | 137/14 |
| 5,337,822 A | | 8/1994 | Massie et al. | 166/264 |
| 5,338,514 A | * | 8/1994 | Morabito et al. | 422/89 |
| 5,377,755 A | | 1/1995 | Michaels et al. | 166/264 |
| 5,803,951 A | * | 9/1998 | Wada et al. | 95/22 |
| 5,997,615 A | * | 12/1999 | Luong et al. | 96/105 |
| 6,063,166 A | | 5/2000 | Wilson | |
| 6,074,461 A | | 6/2000 | Wilson | |

(Continued)

FOREIGN PATENT DOCUMENTS

WO    00/36482 A1    6/2000

(Continued)

OTHER PUBLICATIONS

Zuttel, A. "Materials for Hydrogen Storage." *Materials Today*, Sep. 2003: p. 24-33.

*Primary Examiner*—Duane Smith
*Assistant Examiner*—Robert A Clemente
(74) *Attorney, Agent, or Firm*—Steven McHugh; James McAleenan; Jody Lynn DeStefanis

(57) ABSTRACT

A self-contained chromatography system is provided and includes a chromatography column, a carrier gas reservoir containing a carrier gas and an analyte stream processing device, wherein the carrier gas reservoir is disposed upstream from the chromatography column and wherein the analyte stream processing device is disposed downstream from the chromatography column. A method for implementing the self-contained chromatography system is also provided and includes generating a first system pressure upstream from the chromatography column and a second system pressure downstream from the chromatography column to cause the carrier gas to flow between the carrier gas reservoir and the analyte stream processing device. The method further includes combining a sample material with the carrier gas, introducing the combined sample to the chromatography column to generate the analyte stream and processing the analyte stream via the analyte stream processing device.

26 Claims, 13 Drawing Sheets

U.S. PATENT DOCUMENTS

| | | | |
|---|---|---|---|
| 6,293,995 B2 * | 9/2001 | Wilson | 95/23 |
| 6,306,200 B1 * | 10/2001 | Yu | 96/102 |
| 6,439,307 B1 | 8/2002 | Reinhardt | 166/264 |
| 6,719,826 B2 * | 4/2004 | Sasano et al. | 95/87 |
| 7,135,056 B2 * | 11/2006 | Henderson | 95/82 |
| 7,260,978 B2 * | 8/2007 | Miyagawa | 73/23.37 |

FOREIGN PATENT DOCUMENTS

| | | |
|---|---|---|
| WO | WO01/73424 A1 | 4/2001 |

* cited by examiner

SELF-CONTAINED CHROMATOGRAPHY SYSTEM

FIELD OF THE INVENTION

This disclosure relates generally to the evaluation of fluids, and more particularly to the determination of the composition of fluids using a self-contained chromatography system.

BACKGROUND OF THE INVENTION

Hydrocarbon producing fields typically include a subterranean fluid that is comprised of a mixture of oil, gas and water, wherein the phase relationship between these components are controlled by the pressure, temperature and composition of the fluid. It is desirable to analyze and evaluate these fluids to determine a variety of fluid characteristics of commercial interest to the petroleum industry, such as the type and quality of the fluid within the reservoir. One way to accomplish this is by retrieving a sample of the subterranean formation fluid to the surface and analyzing the fluid to determine its composition using known techniques, such as gas chromatography.

Gas chromatography is a well-known method for identifying the chemical composition of a material sample and has found application in a variety of industries which rely on the identification of chemical compounds, such as the petroleum industry which uses chromatography to identify the chemical composition making up a subterranean fluid to be extracted. The gas chromatography process involves vaporizing and introducing a material sample into a chromatographic column, wherein the material sample is transported through the column by the flow of an inert, gaseous mobile phase, such as nitrogen ($N_2$), hydrogen ($H_2$) or Helium (He). Although the material sample is transported through the column via the carrier gas, the motion of the analyte is inhibited by the adsorption of the analyte molecules onto a stationary phase.

There are at least two well-known types of columns typically in use with gas chromatography systems: packed columns and capillary columns. A packed column contains a finely divided solid support material (eg. diatomaceous earth) which may be coated with a stationary phase, wherein the nature of the coating material is dependent upon the type of materials to be strongly adsorbed. This allows a packed column to be tailored to separate a specific type(s) of compound. A capillary column, on the other hand, has a very small internal diameter (on the order of tenths of millimeters) and the column walls are coated with the active materials. For example, most capillary columns are made of fused-silica with a polyimide outer coating, or stainless steel, and tend to be flexible, allowing for a very long column which can be wound into a small coil.

As such, the rate at which the molecules progress along the column depends upon the strength of the adsorption, which in turn depends upon the type of molecule and the column material. Since each type of molecule has a different rate of progression, the various components of the sample material are separated as they progress along the column and thus reach the end of the column at different times. A detection device is then used to monitor the outlet stream of analytes from the column to determine the amount of analyte exiting the column as well as the time it takes for the analyte to traverse the column. These substances may then be generally identified by the order in which they emerge from the column and by the residence time of the analyte within the column.

Unfortunately however, the retrieval of formation fluids from a subterranean reservoir to the surface may have undesirable consequences. For example, after samples of petroleum fluids are extracted from the earth formation at high temperature and high pressure, they must be brought to the surface, transferred to a transportation vessel and shipped to a distant laboratory for analysis. Changing temperatures and pressures associated with these operations can lead to changes in the fluids, some of which are irreversible. Additionally, leaks in the pressure vessel and transfers between pressure vessels also tend to change the composition of the fluid. These significant and irreversible changes in the fluid characteristics reduce the ability to accurately evaluate the actual properties of the formation fluid.

Another undesirable consequence involving the retrieval of formation fluids from a subterranean reservoir to the surface includes the time and cost involved in running a sampling tool to the formation of interest, retrieving a sample of the fluid within the formation and analyzing the sample of fluid without affecting the integrity of the composition of the fluid. One way to accomplish this involves maintaining the pressure of the formation fluid sample using various apparatus, see U.S. Pat. No. 5,337,822 (1994) to Massie et al., U.S. Pat. No. 5,303,775 (1994) to Michaels et al., U.S. Pat. No. 5,377,755 (1995) to Michaels et al., and U.S. Pat. No. 6,439,307 (2002) to Reinhardt, incorporated by reference herein in their entireties.

One way to accomplish the desired analysis of formation fluids without compromising the integrity of the fluid composition involves the down-hole characterization of formation fluids using borehole chromatography techniques, see U.S. Pat. No. 4,739,654 (1988) to Pilkington et al. and PCT Pat. Appl No. PCT/US01/40372 (2001) to Storm and Richardson. This may be accomplished by disposing a downhole chromatograph within a well bore and by introducing a sample fluid into the chromatograph, wherein the chromatograph may be powered via an umbilical (i.e. a wireline from the surface), a down-hole turbine/alternator power supply or via a battery device. The chromatograph would then analyze the composition of the formation fluid sample and communicate the results to the surface. Unfortunately, however, several problems still exist with current downhole chromatography devices and techniques. For example, while U.S. Pat. No. 4,739,654 (1988) to Pilkington et al. allegedly discloses a downhole chromatography technique, the method and apparatus disclosed therein cannot be implemented in the field, as they suffer from severe defects, namely inadequate gas handling storage and disposal techniques.

One problem involves the handling of the carrier gas. In conventional gas chromatography systems, the carrier gas is a consumable that is typically provided from a high pressure tank, allowed to flow through the column and vented into the atmosphere, wherein the flow rate of the gas through the column must be constant in order to produce interpretable chromatograms. In laboratory and other surface systems, the constant flow rate through the column is ensured by maintaining a constant pressure drop along the column, wherein a gas regulator is used to control the flow line pressure at the high pressure end of the column and the low pressure end of the column is vented at ambient atmospheric pressure. Unfortunately, this type of carrier gas system is not suitable for borehole application for several reasons.

First, the use of consumable gases in wireline, logging while drilling (LWD) or subsea tools is currently undesirable because they require delivery of these gases to shops and depots. Moreover, when tools are required for multiple jobs at remote sites, e.g. offshore platforms, the logistics of delivery become even more troublesome. Second, in the absence of contact with the atmosphere, there is no infinite reservoir for the disposal of the carrier gas once it has traversed the column. Third, current systems and methods are not capable of maintaining a constant pressure gradient along the chromatography column.

Accordingly, it is an object of the present invention to provide a self-contained chromatography system capable of sample analysis in remote locations. It is a further object of the present invention to provide a self-contained chromatography system for down-hole sample analysis. It is yet a further object of the present invention to provide a chromatography system having an improved gas handling system. Furthermore, it is yet another object of the present invention to provide a chromatography technique having an improved pressure regulation means at the outlet of the gas chromatography system.

SUMMARY OF THE INVENTION

A self-contained chromatography system is provided and includes a chromatography device configured to combine a material sample to be analyzed and a carrier gas, wherein the chromatography device processes the combination of the material sample and the carrier gas to generate an analyte stream. Additionally, a carrier gas reservoir for containing the carrier gas at a first system pressure is provided, wherein the carrier gas reservoir is disposed upstream from the chromatography device. An analyte stream processing device is also provided wherein the analyte stream processing device is disposed downstream from the chromatography device to receive and process the analyte stream at a second system pressure, wherein the first system pressure is greater than the second system pressure to cause the analyte stream to flow through the chromatography column at a desired flow rate.

A method for implementing a self-contained chromatography system is described, wherein the self-contained chromatography system includes a chromatography column, a carrier gas reservoir containing a carrier gas and an analyte stream processing device. The carrier gas reservoir is disposed upstream from the chromatography column and the analyte stream processing device being disposed downstream from the chromatography column. The method further includes generating a first system pressure upstream from the chromatography column and a second system pressure downstream from the chromatography column such that a pressure gradient exists between the first system pressure and the second system pressure to cause the carrier gas to flow between the carrier gas reservoir and the analyte stream processing device at a predetermined flow rate. The method further includes combining a sample material with the carrier gas to generate a combined sample and introducing the combined sample to the chromatography column to generate the analyte stream, wherein the combined sample traverses the chromatography column at the predetermined flow rate. The method also includes introducing the analyte stream into the analyte stream processing device at the predetermined flow rate and processing the analyte stream via the analyte stream processing device.

A method for implementing a self-contained chromatography system is also described, wherein the self-contained chromatography system includes a carrier gas reservoir containing a carrier gas and wherein the carrier gas reservoir is disposed upstream from a chromatography column is provided. The method includes combining a sample material with the carrier gas to generate a combined sample and introducing the combined sample to the chromatography column to generate an analyte stream. The method also includes generating a first system pressure upstream from the chromatography column and a second system pressure downstream from the chromatography column such that a pressure gradient exists between the first system pressure and the second system pressure to cause the combined sample to traverse the chromatography column at a predetermined flow rate. Moreover, the method includes processing the analyte stream to flow through the self-contained chromatography system at the predetermined flow rate.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike.

DETAILED DESCRIPTION

In accordance with the present invention, the disadvantages discussed hereinabove may be addressed via a remotely operable self-contained gas chromatography system (GCS) capable of maintaining a desired rate of carrier gas flow through the GCS column and/or adequately handling the carrier gas following traversal of the GCS column. As disclosed herein, it is contemplated that maintaining a desired rate of carrier gas flow through the GCS column may be accomplished via a variety of methods and/or devices, such as using pressure regulators, flow pumps and/or "pressure reservoirs," such as fixed temperature metal hydride reservoirs. Furthermore as disclosed herein, it is contemplated that the adequate handling of the carrier gas following traversal of the GCS column may be accomplished by using a variety of methods and/or devices, such as a filter, a waste vessel, a flow line for expelling the used carrier gas and/or a carrier gas purification device, such as an oxidation/electrolysis device.

One approach that may be used to maintain a desired rate of carrier gas flow through the GCS column may involve using a "pressure reservoir" or isobaric (constant pressure) reservoir which may be comprised of metal hydride materials, wherein the reservoir may be disposed upstream and/or downstream to the chromatography column. This type of reservoir may be useful because metal hydride materials (which store hydrogen at high density) readily adsorb and/or desorb hydrogen responsive to a variety of factors, such as temperature and/or pressure. Metal hydrides are typically alloys of transition and/or rare earth metals that form compounds or mixtures of compounds that have a continuously varying hydrogen content, often referred to as the hydrogen-to-metal ratio (H/M), that is dependent upon the temperature and the pressure of the hydrogen gas that is in contact with the metal hydride material.

Figure 1:
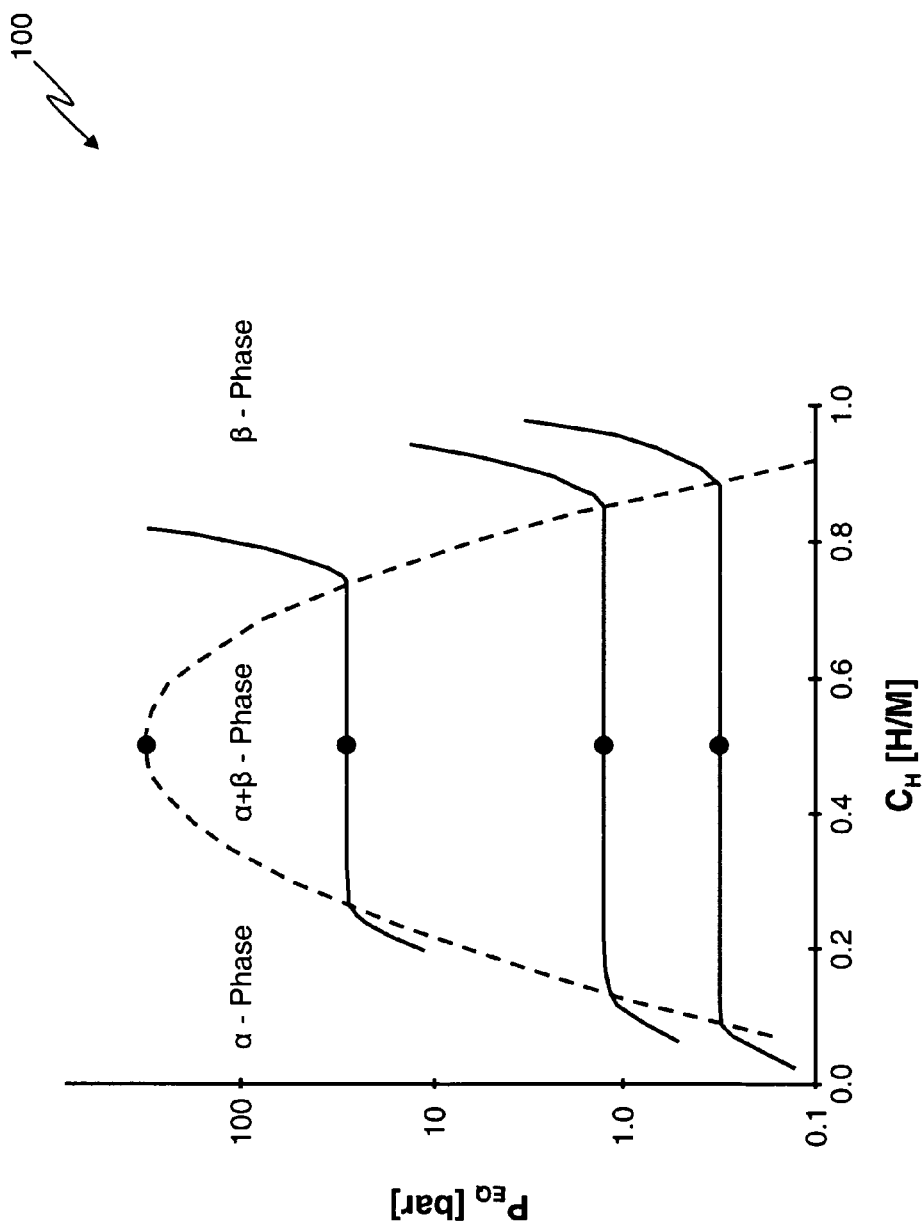
FIG. 1 is a graph illustrating properties of hydrogen isotherms for low temperature metal hydride.

These adsorption/desorption properties can be seen by referring to FIG. 1, which shows a composition diagram 100 for a metal hydride material disposed in an environment having a variable amount of hydrogen for three (3) fixed temperature levels, wherein the composition diagram 100 includes several regions which illustrate the effect of pressure P on the hydrogen-to-metal ratio (H/M) of the metal hydride material disposed in the environment. As shown, the composition diagram 100 is divided into three (3) phase regions based upon the hydrogen-to-metal ratio (H/M): an α-phase region, a (α+β)-phase region and a β-phase region.

While in the α-phase region, the hydrogen-to-metal ratio (H/M) is relatively low. However, as the hydrogen pressure P of the reservoir increases, the metal hydride material adsorbs hydrogen causing the hydrogen-to-metal ratio (H/M) to increase. In a similar fashion, while in the β-phase region, as hydrogen gas is added to the reservoir, the hydrogen pressure P of the reservoir also increases and the metal hydride material again adsorbs hydrogen causing the hydrogen-to-metal ratio (H/M) to increase accordingly and if hydrogen gas is continually added to the reservoir, then eventually the hydrogen will occupy every possible site in the metal hydride material after which no further hydrogen can be adsorbed and the hydrogen-to-metal ratio (H/M) will be maximized.

On the other hand, while in the (α+β) phase region, although addition of hydrogen gas to the reservoir causes the hydrogen-to-metal ratio (H/M) to increase, the metal hydride material maintains a constant hydrogen pressure, or plateau pressure, within the reservoir, wherein the magnitude of this plateau pressure is dependent upon the temperature of the reservoir and the type of metal hydride material being used. As such, when hydrogen gas is added to the reservoir, the metal hydride material continues to maintain a constant gas pressure in the reservoir by continuously adsorbing hydrogen. Conversely, when hydrogen gas is withdrawn from the reservoir, the metal hydride material maintains a constant gas pressure in the reservoir by continuously desorbing hydrogen.

Figure 2:
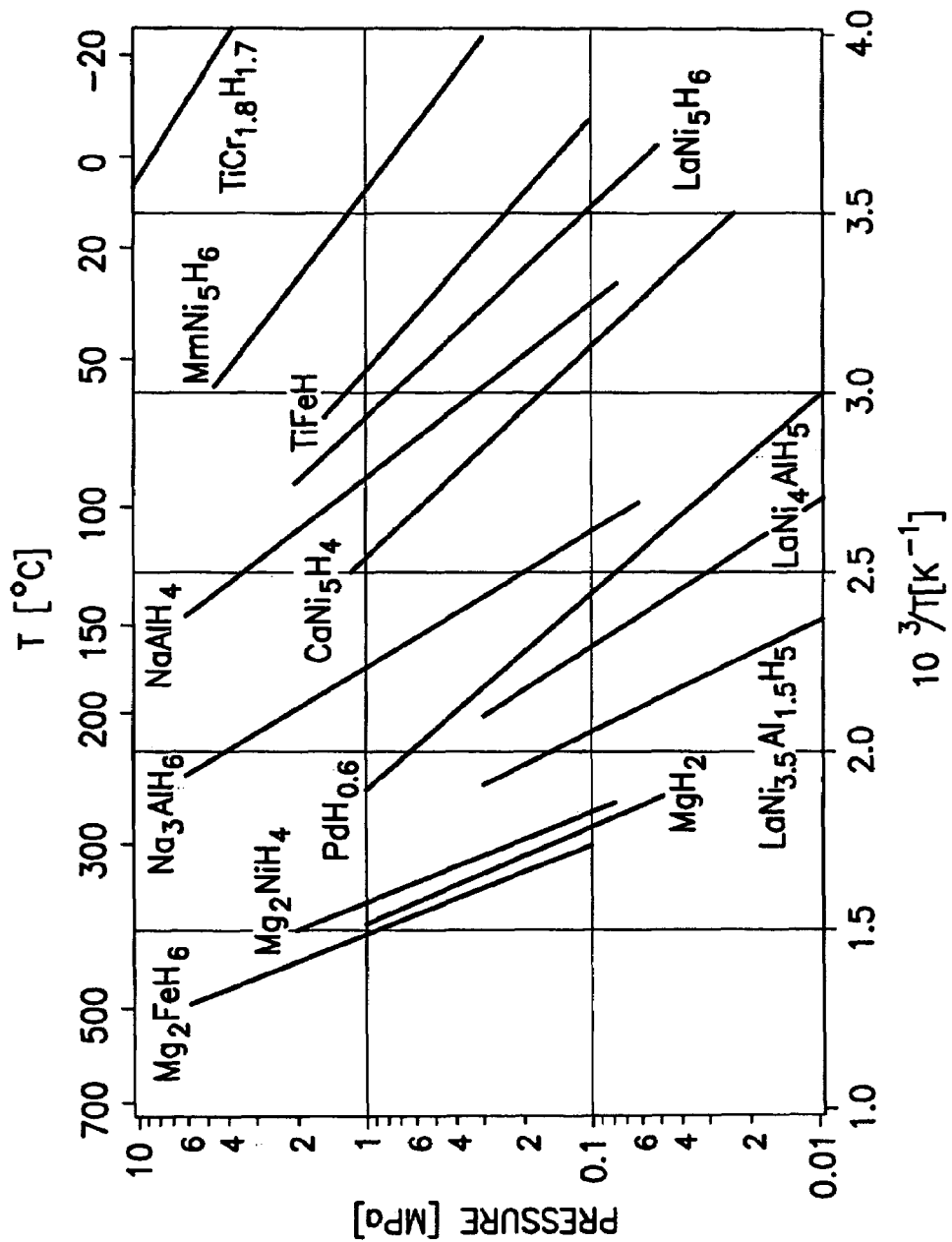
FIG. 2 is a graph illustrating temperature and pressure composition plateaus for various metal hydrides.

It is well known that the operation of a gas chromatography system requires a known flow rate and one way to ensure this flow rate is by controlling the pressures upstream and/or downstream from the gas chromatography column. Because the flow rates are sometimes varied, changing according to a predetermined or controlled program, these pressures may also be varied. One way to vary the pressure of hydrogen gas in contact with a metal hydride is by varying the temperature of the reservoir. This is possible because as the reservoir temperature increases, the plateau of the metal hydride phase diagram moves to higher pressure, as shown in FIG. 2. Thus, metals used in the upstream and/or downstream gas reservoirs should be selected according to their temperature-dependent isobars or plateau pressures. However, although it is relatively easy to raise the temperature of downhole tool components above the ambient temperature by means of resistance heaters, it is relatively difficult to lower the temperature of downhole tool components below the ambient temperature. Thus, the metal hydrides that have desirable properties above the maximum expected ambient temperature should be considered suitable candidates. For example, consider a downhole gas chromatography system that must operate at ambient temperatures up to 200° C., wherein the downstream reservoir of the chromatograph is to be maintained at a constant pressure of one atmosphere (0.1 MPa) pressure. Referring to FIG. 2, which shows the temperature and pressure of composition plateaus for various metal hydrides, it appears that $LaNi_{3.5}Al_{1.5}$ is in equilibrium with hydrogen gas at 0.1 MPa at a temperature of approximately 210° C. As such, given the above constraints, $LaNi_{3.5}Al_{1.5}$ would be a candidate for the downstream reservoir.

Figure 3:
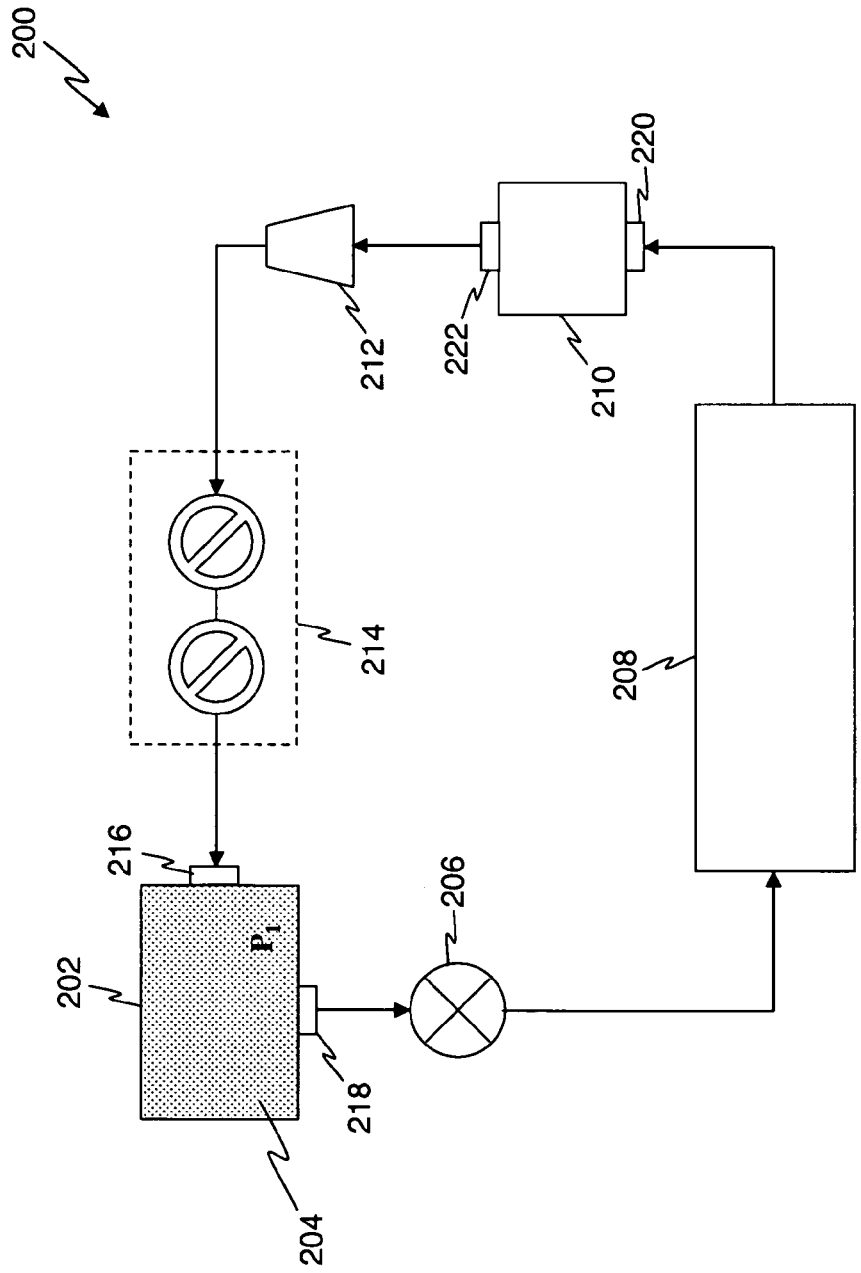
FIG. 3 is a schematic block diagram illustrating a first embodiment of a self-contained chromatography system.

In light of the above discussion, the property of metal hydride materials of maintaining a constant pressure over a range of hydrogen-to-metal ratios (H/M) for a fixed temperature may be used to create fixed temperature isobaric reservoirs that may be used to maintain desired pressure(s) upstream and/or downstream from a chromatography column. Referring to FIG. 3, a first embodiment of a self-contained chromatography system 200 which maintains a constant carrier gas pressure upstream and/or downstream of a chromatography column is shown and includes a first carrier gas reservoir 202 for containing a carrier gas 204 at a first pressure $P_1$, a pressure regulation device 206, a gas chromatography device 208, a second carrier gas reservoir 210, a pumping device 212 and a filtration device 214, wherein the first carrier gas reservoir 202 includes a first carrier gas reservoir inlet 216 and a first carrier gas reservoir outlet 218 and wherein the second carrier gas reservoir 210 includes a second carrier gas reservoir inlet 220 and a second carrier gas reservoir outlet 222. The self-contained chromatography system 200 is configured such that the first carrier gas reservoir outlet 218 is in flow communication with the second carrier gas reservoir inlet 220 via the pressure regulation device 206 and the gas chromatography device 208 and such that the second carrier gas reservoir outlet 222 is in flow communication with the first carrier gas reservoir inlet 216 via the pumping device 212 and the filtration device 214.

Figure 4:
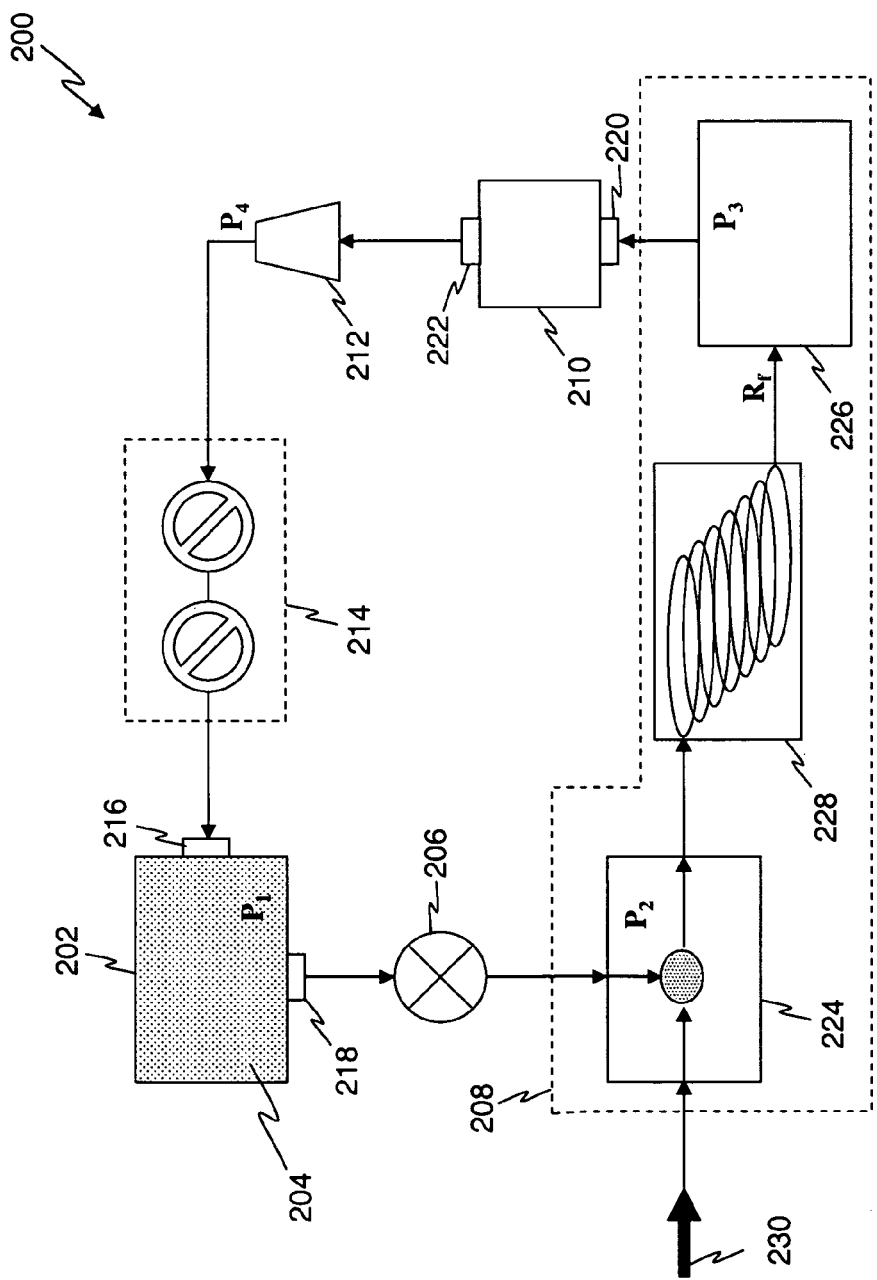
FIG. 4 is a schematic block diagram illustrating the self-contained chromatography system in FIG. 3.

Referring to FIG. 4, the gas chromatography device 208 may include an injector device 224 that is in flow communication with a detection device 226 via a chromatography column 228. As shown, the injector device 224 is configured to receive a sample substance 230 to be analyzed and the carrier gas 204 from the first carrier gas reservoir outlet 218 via the pressure regulation device 206 which creates a second pressure $P_2$ within the injector device 224, wherein the first pressure $P_1$ is greater than the second pressure $P_2$ such that the pressure gradient between $P_1$ and $P_2$ allows the carrier gas 204 to controllably flow into the injector device 224. It should be appreciated that the pressure regulation device 206 may be an optional device and may be provided to better control the flow rate through the chromatography column 228. The combined sample substance 230 and carrier gas 204 may then be introduced into the chromatography column 228 and the analyte stream output $R_f$ from the chromatography column 228 is detected by the detection device 226 which generates data responsive to the analyte stream output $R_f$. The detection device 226 and/or the chromatography column 228 may be configured to introduce the analyte stream output $R_f$ into the second carrier gas reservoir 210 via the second carrier gas reservoir inlet 220.

It should be appreciated that the second carrier gas reservoir 210 includes a predetermined metal hydride material that is maintained at a predetermined temperature responsive to the metal hydride material to generate a third pressure $P_3$, wherein the third pressure $P_3$ is lower than the second pressure $P_2$ such that the pressure gradient between $P_2$ and $P_3$ allows the analyte stream $R_f$ to controllably flow through the chromatography column 228 and into the second carrier gas reservoir 210. The pumping device 212 may then be operated to generate a fourth pressure $P_4$ between the pumping device 212 and the first carrier gas reservoir 202, wherein the fourth pressure $P_4$ is greater than the first pressure $P_1$ such that the pressure gradient between $P_4$ and $P_1$ allows the analyte stream $R_f$ to controllably flow through the filtration device 214 which filters out and retains any contaminants and/or impurities from the analyte stream $R_f$ and the remaining carrier gas is allowed to flow into the first carrier gas reservoir 202.

It should be appreciated that at least one of the first carrier gas reservoir 202 and the second carrier gas reservoir 210 may be an isobaric reservoir that is at least partially comprised of a class of materials that controllably adsorbs/desorbs a carrier gas, such as hydrogen. This class of materials may include any material and/or combination of materials suitable to the desired end purpose, such as a powdered and/or sintered metal hydride material.

Another approach that may be used to maintain a desired rate of carrier gas flow through a chromatography column may involve using an oxidation cell to maintain a low pressure at the downstream end of the chromatography column by burning the effluent (the analyte and a carrier gas, such as hydrogen) from the chromatography column. For example, when the carrier gas is hydrogen, the effluent will be overwhelmingly comprised of hydrogen and the product of the combustion will be primarily water. As such, during the combustion process, the hydrogen and carbon in the analyte are oxidized into water and carbon dioxide, respectively. Additionally, sulfur and nitrogen oxides may be left behind as gas phase contaminants and oxides of trace metals, such as nickel and vanadium, may be left behind as solids. The solids may then be filtered and the water may be separated from the gas phase contaminants via a condenser and pumped into an electrolysis cell, wherein the small volume of contaminant gases and solids may remain in the oxidation cell. The electrolysis cell then breaks down the water into hydrogen and oxygen and a standard two-arm electrolysis cell may be used to collect the gaseous products separately. The hydrogen may then be reused as a carrier gas and the oxygen may be returned to the oxidation cell for future oxidation.

Figure 5:
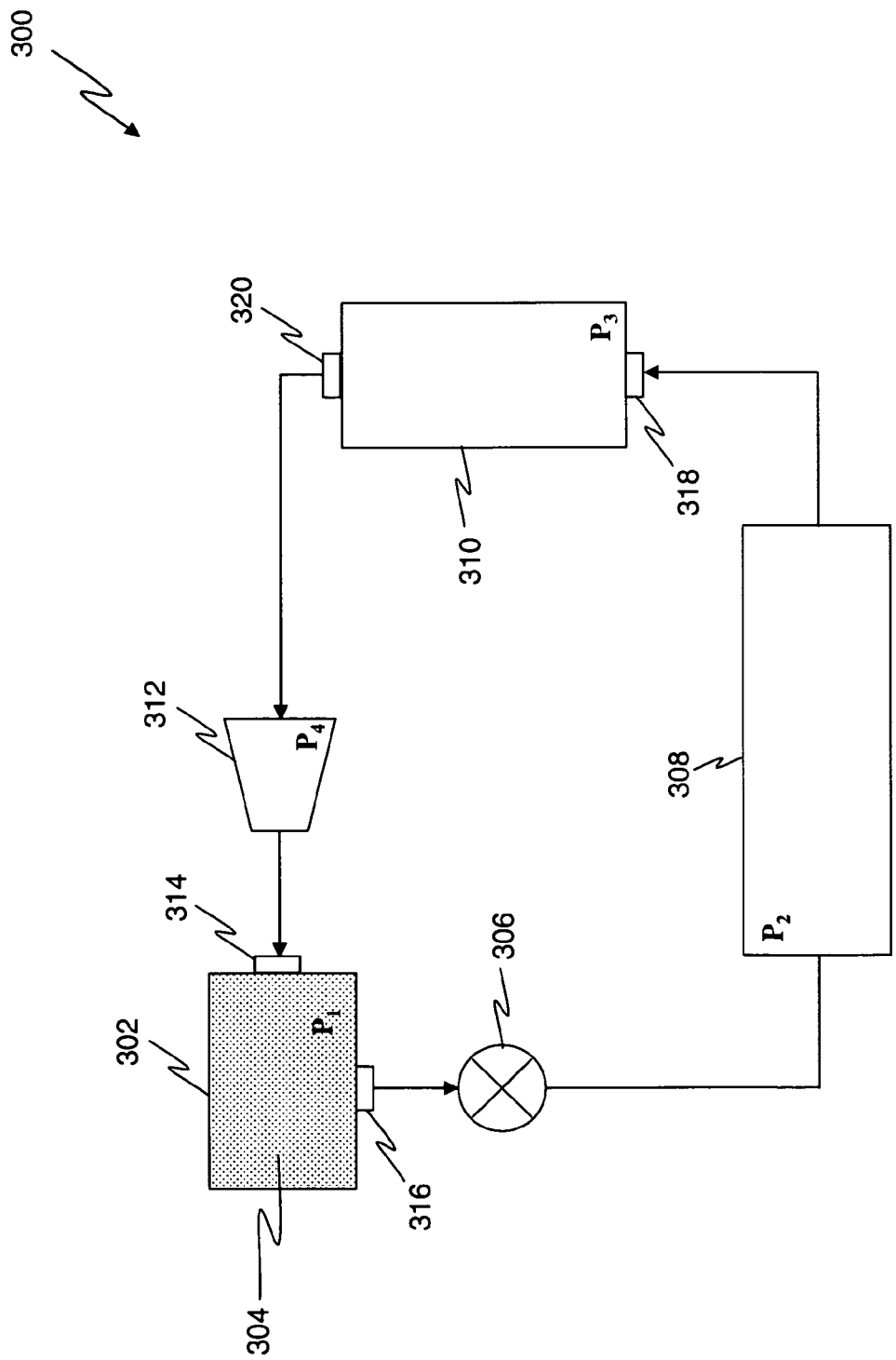
FIG. 5 is a schematic block diagram illustrating a second embodiment of a self-contained chromatography system.

Referring to FIG. 5, a second embodiment of a self-contained chromatography system 300 which maintains a constant carrier gas pressure upstream and/or downstream of the chromatography column is shown and includes a carrier gas reservoir 302 for containing a carrier gas 304 at a carrier gas reservoir pressure $P_1$, a pressure regulation device 306, a gas chromatography device 308, an oxidation/electrolysis device 310 and a pumping device 312, wherein the carrier gas reservoir 302 includes a carrier gas reservoir inlet 314 and a carrier gas reservoir outlet 316 and wherein the oxidation/electrolysis device 310 includes an oxidation/electrolysis device inlet 318 and an oxidation/electrolysis device outlet 320. The self-contained chromatography system 300 is configured such that the first carrier gas reservoir outlet 316 is in flow communication with the oxidation/electrolysis device inlet 318 via the pressure regulation device 306 and the gas chromatography device 308 and such that the oxidation/electrolysis device outlet 320 is in flow communication with the carrier gas reservoir inlet 314 via the pumping device 312.

Figure 6:
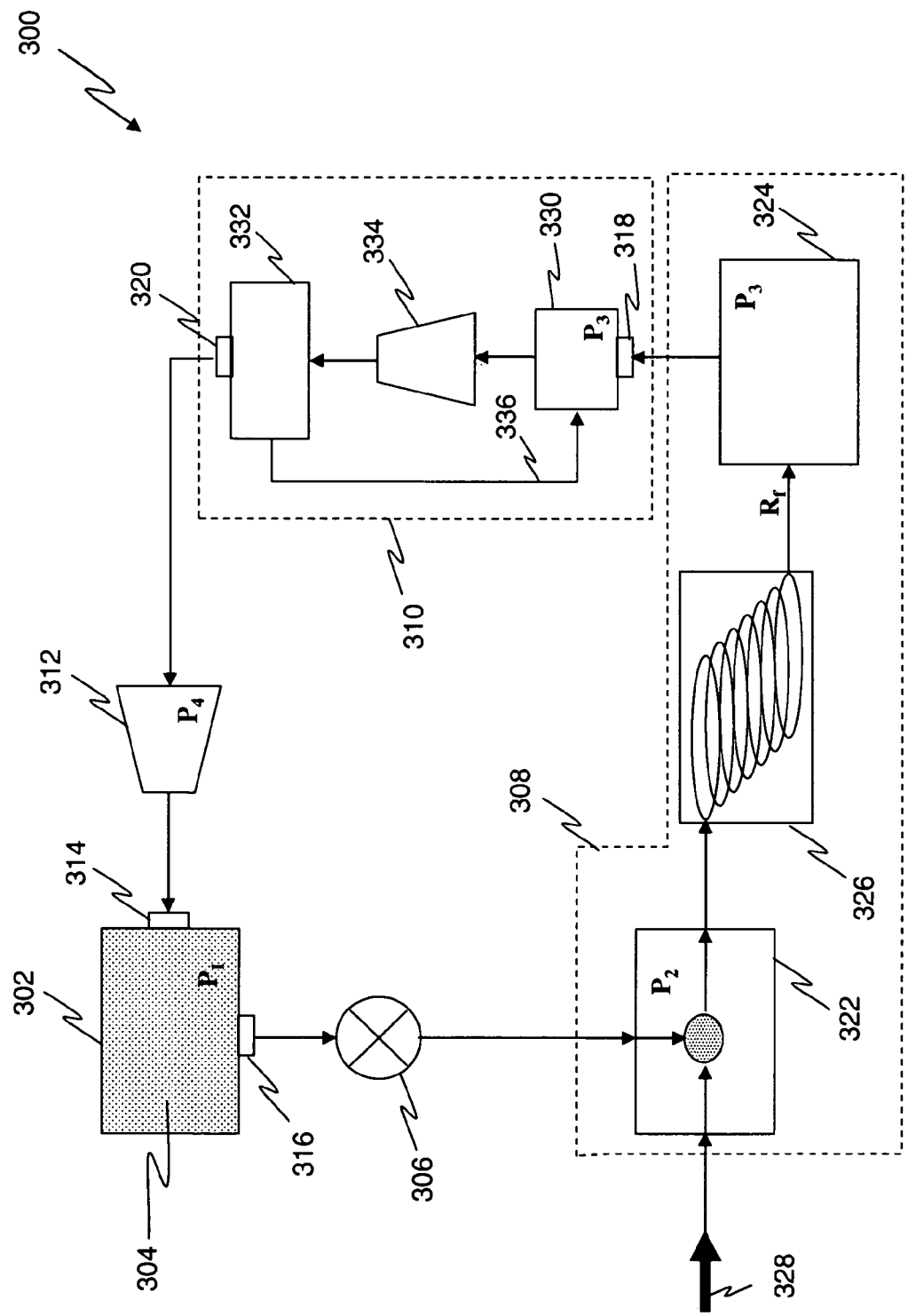
FIG. 6 is a schematic block diagram illustrating the self-contained chromatography system in FIG. 5.

Referring to FIG. 6, the gas chromatography device 308 may include an injector device 322 that is in flow communication with a detection device 324 via a chromatography column 326. As shown, the injector device 322 is configured to receive a sample substance 328 to be analyzed and the carrier gas 304 from the carrier gas reservoir outlet 316 via the pressure regulation device 306 which creates a second pressure $P_2$ within the injector device 322, wherein the first pressure $P_1$ is greater than the second pressure $P_2$ such that the pressure gradient between $P_1$ and $P_2$ allows the carrier gas 306 to controllably flow through the pressure regulation device 306 and into the injector device 322. It should be appreciated that the pressure regulation device 306 may be an optional device and may be provided to better control the flow rate through the chromatography column 326. The combined sample substance 328 and carrier gas 304 may then be introduced into the chromatography column 326 and the analyte stream output $R_f$ from the chromatograph 326 is detected by the detection device 324 which generates data responsive to the analyte stream output $R_f$. The detection device 324 and/or the chromatography column 326 may be configured to introduce the analyte stream output $R_f$ into the oxidation/electrolysis device 310 via the oxidation/electrolysis device inlet 318, wherein the oxidation/electrolysis device 310 may include an oxidation cell 330 that is in flow communication with an electrolysis cell 332 via a water pump 334 and via an oxygen return path 336.

In similar fashion to the first embodiment, the injector device 322 is configured to receive a sample substance 328 to be analyzed and the carrier gas 304 from the carrier gas reservoir outlet 316 via the pressure regulation device 306. A third pressure $P_3$ is generated downstream to the chromatography column 326, wherein $P_2$ is larger than $P_3$ such that the pressure gradient between $P_2$ and $P_3$ allows the analyte stream to controllably flow through the chromatography column 326, through the detection device 324. The detection device 324 and/or the chromatography column 326 may be configured to introduce the analyte stream output $R_f$ into the oxidation cell 330 via the oxidation/electrolysis device inlet 318.

When the analyte stream output $R_f$ is introduced into the oxidation cell 330 the analyte stream $R_f$ interacts with the oxygen contained within the oxidation cell 330 causing an oxidation reaction resulting in a release of energy (i.e. combustion). As such, the hydrogen and carbon in the analyte stream $R_f$ are oxidized into water and carbon dioxide, respectively, while additional solids, such as nickel and vanadium, and gas phase contaminants, such as sulfur and nitrogen oxides, are also produced. The water is separated from the solids via a filtering device within the oxidation cell 330 and the gas phase contaminants via a phase separation device within the oxidation cell 330, such as a condenser and the water is directed to flow into the electrolysis cell 332 via the water pump 334. The small volume of solids and contaminant gases remain in the combustion chamber of the oxidation cell 330. The water is then broken down into hydrogen and oxygen and a standard two-arm electrolysis cell is used to collect the hydrogen and oxygen separately. The oxygen is then directed back into the oxidation cell 330 via the oxygen return path 336 for reuse in future oxidation and the pumping device 312 may then be operated to generate a fourth pressure $P_4$ between the pumping device 312 and the carrier gas reservoir 302, wherein the fourth pressure $P_4$ is greater than the first pressure $P_1$ such that the pressure gradient between $P_4$ and $P_1$ allows the recovered hydrogen to controllably flow from the electrolysis cell 332 into the carrier gas reservoir 302.

Another approach that may be used to maintain a desired rate of carrier gas flow through a chromatography column may involve using pumping devices, flow control devices and filtration devices to maintain a pressure gradient across the chromatography column and to handle the carrier gas at the downstream end of the chromatography column.

Figure 7:
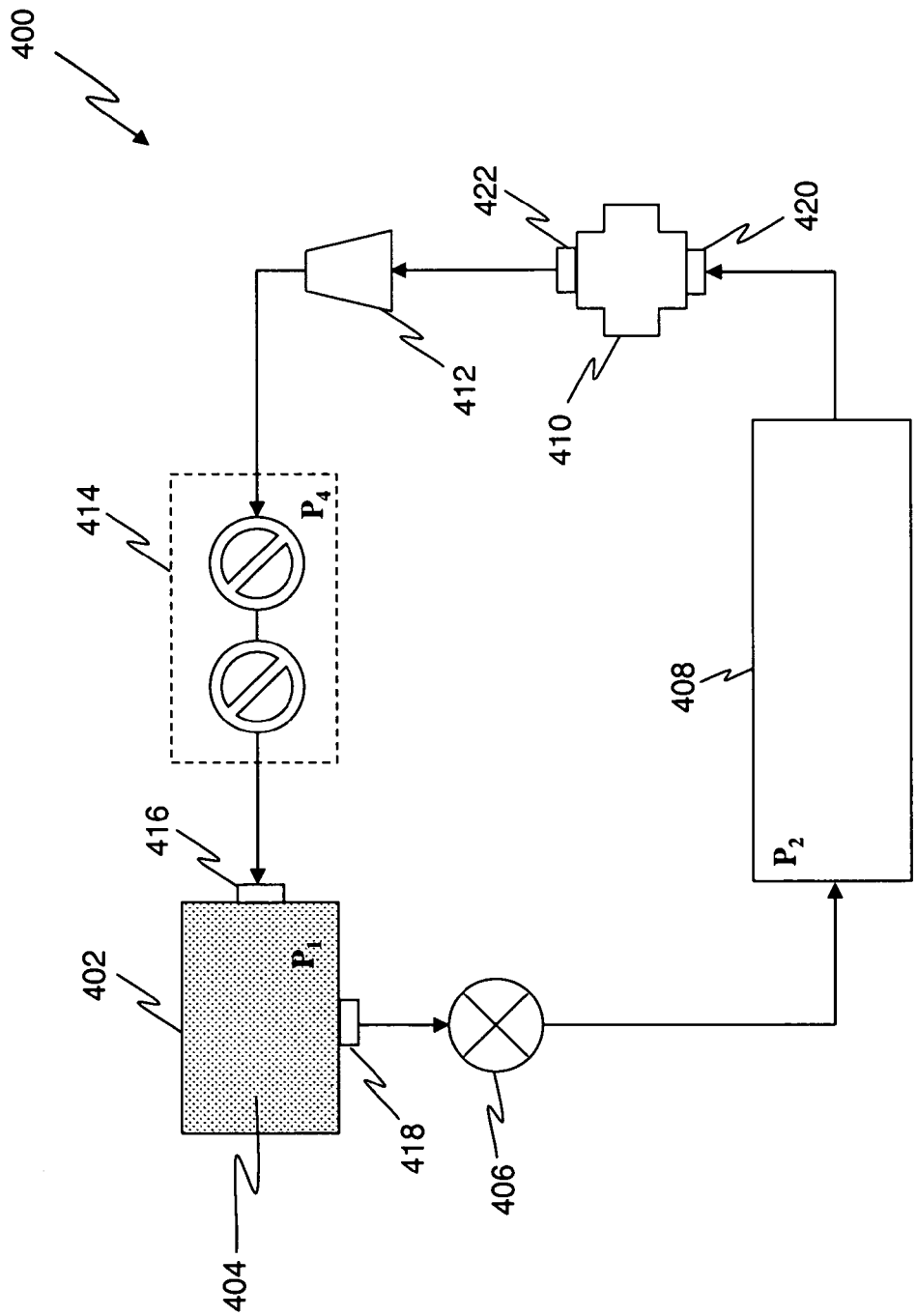
FIG. 7 is a schematic block diagram illustrating a third embodiment of a self-contained chromatography system.

Referring to FIG. 7, a third embodiment of a self-contained chromatography system 400 which maintains a constant carrier gas pressure upstream and/or downstream of the chromatography column is shown in a "closed" system configuration and includes a carrier gas reservoir 402 for containing a carrier gas 404 at a carrier gas reservoir pressure $P_1$, a pressure regulation device 406, a gas chromatography device 408, a flow controller device 410, a pumping device 412 and a filtration device 414, wherein the carrier gas reservoir 402 includes a carrier gas reservoir inlet 416 and a carrier gas reservoir outlet 418 and wherein the flow controller device 410 includes a flow controller device inlet 420 and a flow device outlet 422. The self-contained chromatography system 400 is configured such that the carrier gas reservoir outlet 418 is in flow communication with the flow controller device inlet 420 via the pressure regulation device 406 and the gas chromatography device 408 and such that the flow controller device outlet 422 is in flow communication with the carrier gas reservoir inlet 416 via the pumping device 412 and the filtration device 414.

Figure 8:
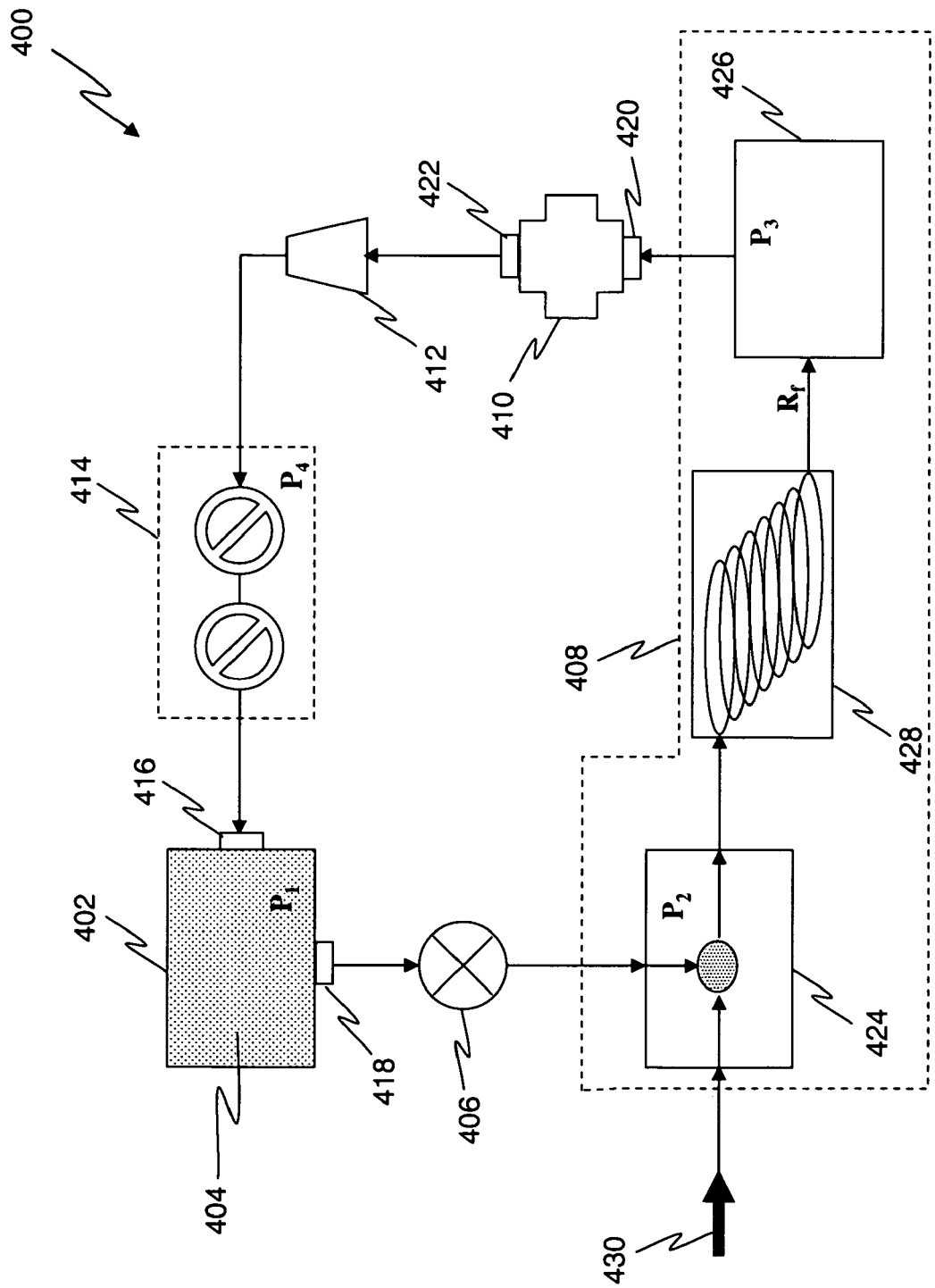
FIG. 8 is a schematic block diagram illustrating the self-contained chromatography system of FIG. 7.

Referring to FIG. 8, the gas chromatography device 408 may include an injector device 424 that is in flow communication with a detection device 426 via a chromatography column 428. As shown, the injector device 424 is configured to receive a sample substance 430 to be analyzed and the carrier gas 404 from the carrier gas reservoir outlet 418 via the pressure regulation device 406 which creates a second pressure $P_2$ within the injector device 424, wherein the first pressure $P_1$ is greater than the second pressure $P_2$ such that the pressure gradient between $P_1$ and $P_2$ allows the carrier gas 404 to controllably flow through the pressure regulation device 406 and into the injector device 424. It should be appreciated that the pressure regulation device 406 may be an optional device and may be provided to better control the flow rate through the chromatography column 428. The combined sample substance 430 and carrier gas 404 may then be introduced into the chromatography column 428 and the flow controller device 410 is operated to generate a third pressure $P_3$ downstream to the chromatography column 428, wherein $P_2$ is larger than $P_3$ such that the pressure gradient between $P_2$ and $P_3$ allows the analyte stream to controllably flow through the chromatography column 428, through the detection device 426 and into the flow controller device 410. The pumping device 412 may then be operated to generate a fourth pressure $P_4$, wherein the fourth pressure $P_4$ is greater than the first pressure $P_1$ such that the pressure gradient between $P_4$ and $P_1$ allows the analyte stream $R_f$ to controllably flow through the filtration device 414 which recovers the carrier gas 404 by filtering out and retaining any contaminants and/or impurities in the analyte stream $R_f$ and directs the carrier gas 404 into the carrier gas reservoir 402 for reuse, wherein any impurities are left within the filtration device 414.

Figure 9:
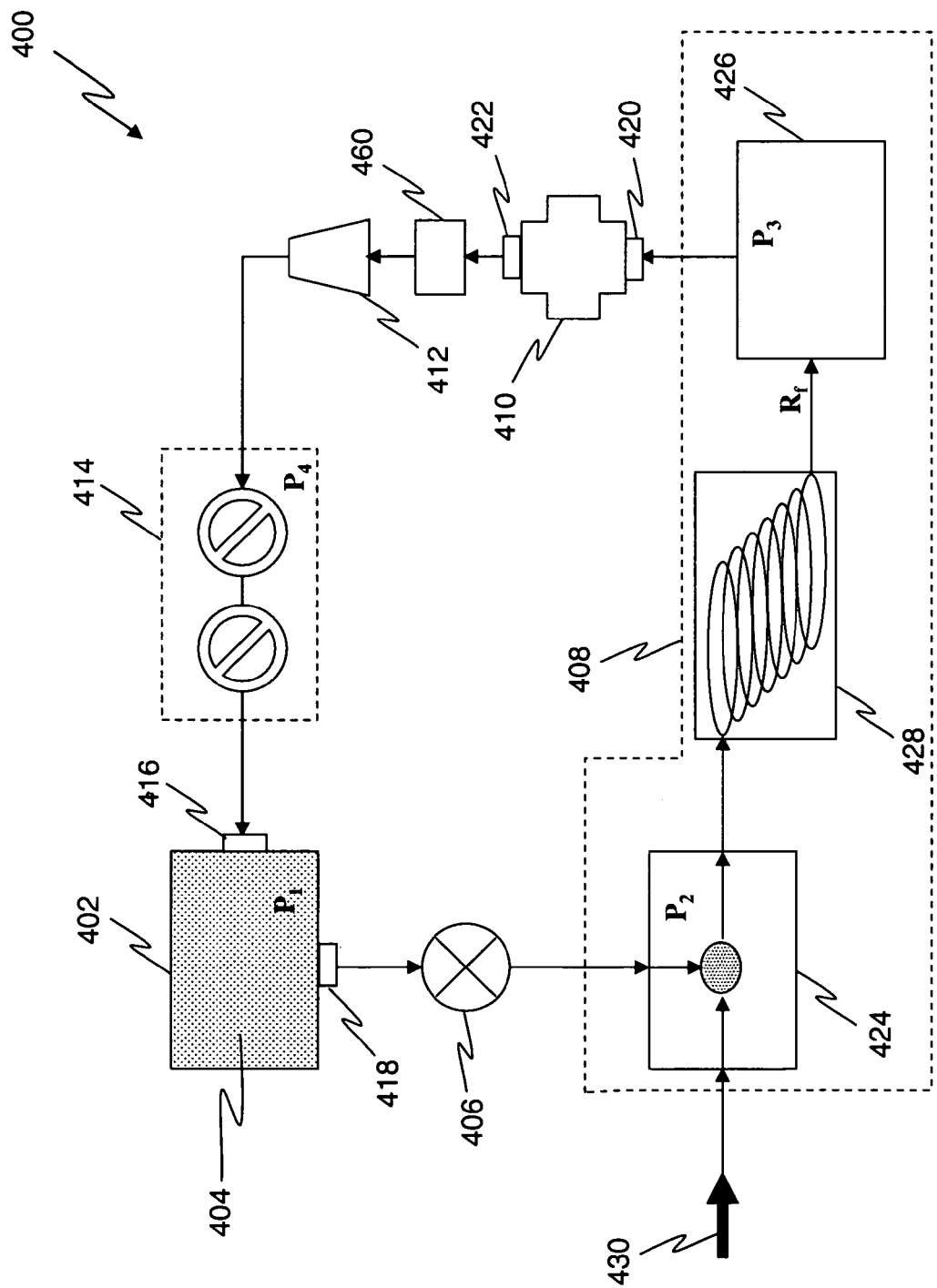
FIG. 9 is a schematic block diagram illustrating the self-contained chromatography system of FIG. 7 having an auxiliary volume.

Referring to FIG. 9, it should be appreciated that an auxiliary reservoir 460 may also be provided and disposed between the flow controller device 410 and the pumping device 412 to act as a damping device and improve the stability of the flow rate. Moreover, the flow controller device 410 and/or chromatography column flow rate may be selected in a manner responsive to the configuration of the chromatography column 428 and/or the detection device 426 such that even if the pressure varies downstream from the flow controller device 410, the desired flow rate through the chromatography column 428 will be maintained.

Figure 10:
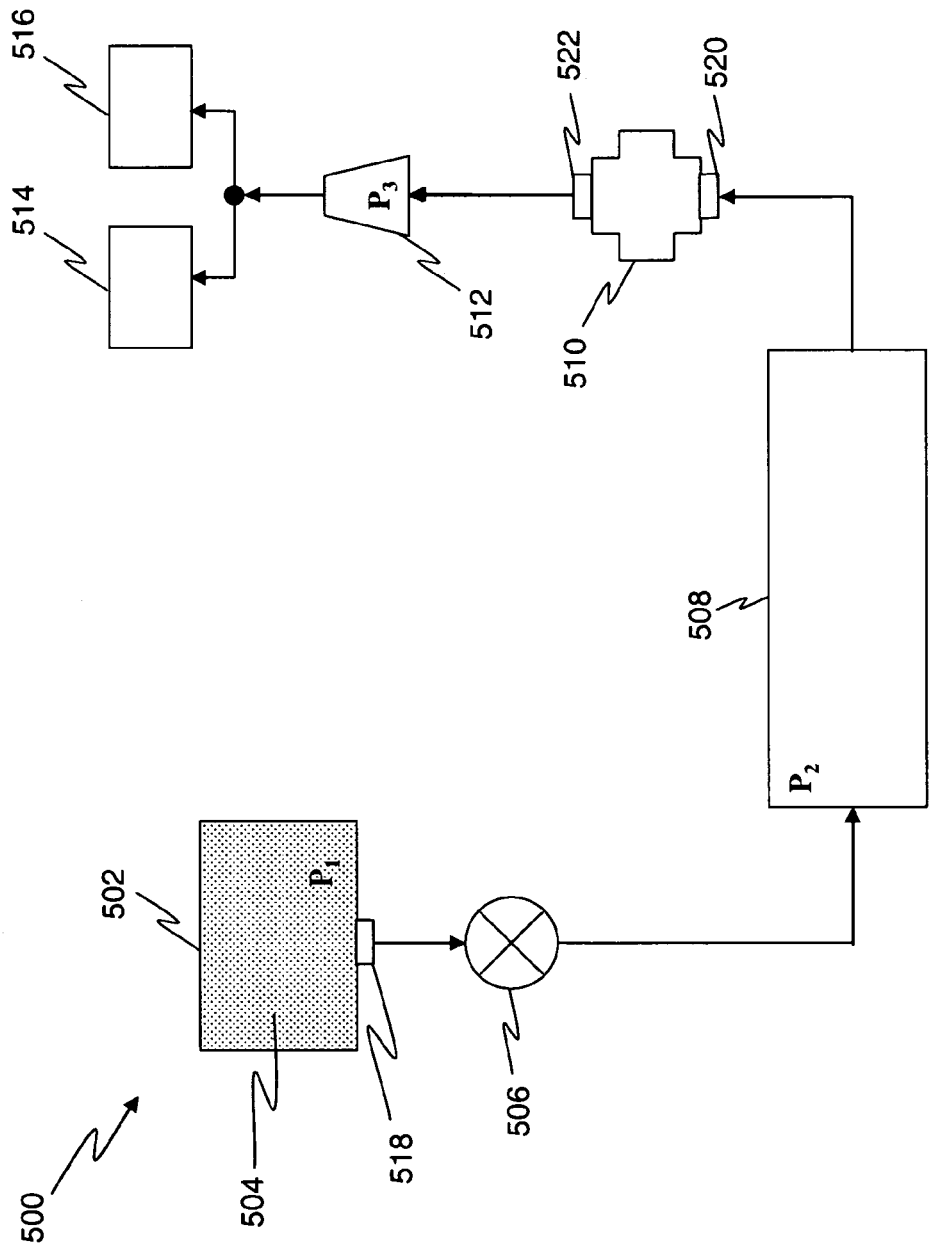
FIG. 10 is a schematic block diagram illustrating a fourth embodiment of a self-contained chromatography system.

Referring to FIG. 10, a fourth embodiment of a self-contained chromatography system 500 which maintains a constant carrier gas pressure upstream and/or downstream of the chromatography column is shown in an "open" system configuration and includes a carrier gas reservoir 502 for containing a carrier gas 504 at a carrier gas reservoir pressure $P_1$, a pressure regulation device 506, a gas chromatography device 508, a flow controller device 510, a pumping device 512, and a waste vessel 514, wherein the waste gas may either be compressed and stored within the waste vessel 514 or the waste gas may be expelled outside of the system 516, respectively. The carrier gas reservoir 502 includes a carrier gas reservoir outlet 518 and the flow controller device 510 includes a flow controller device inlet 520 and a flow controller device outlet 522. The self-contained chromatography system 500 is configured such that the carrier gas reservoir outlet 518 is in flow communication with the flow controller device inlet 520 via the pressure regulation device 506 and the gas chromatography device 508 and such that the flow controller device outlet 522 is in flow communication with the waste vessel 514 and/or the flow line 516.

Figure 11:
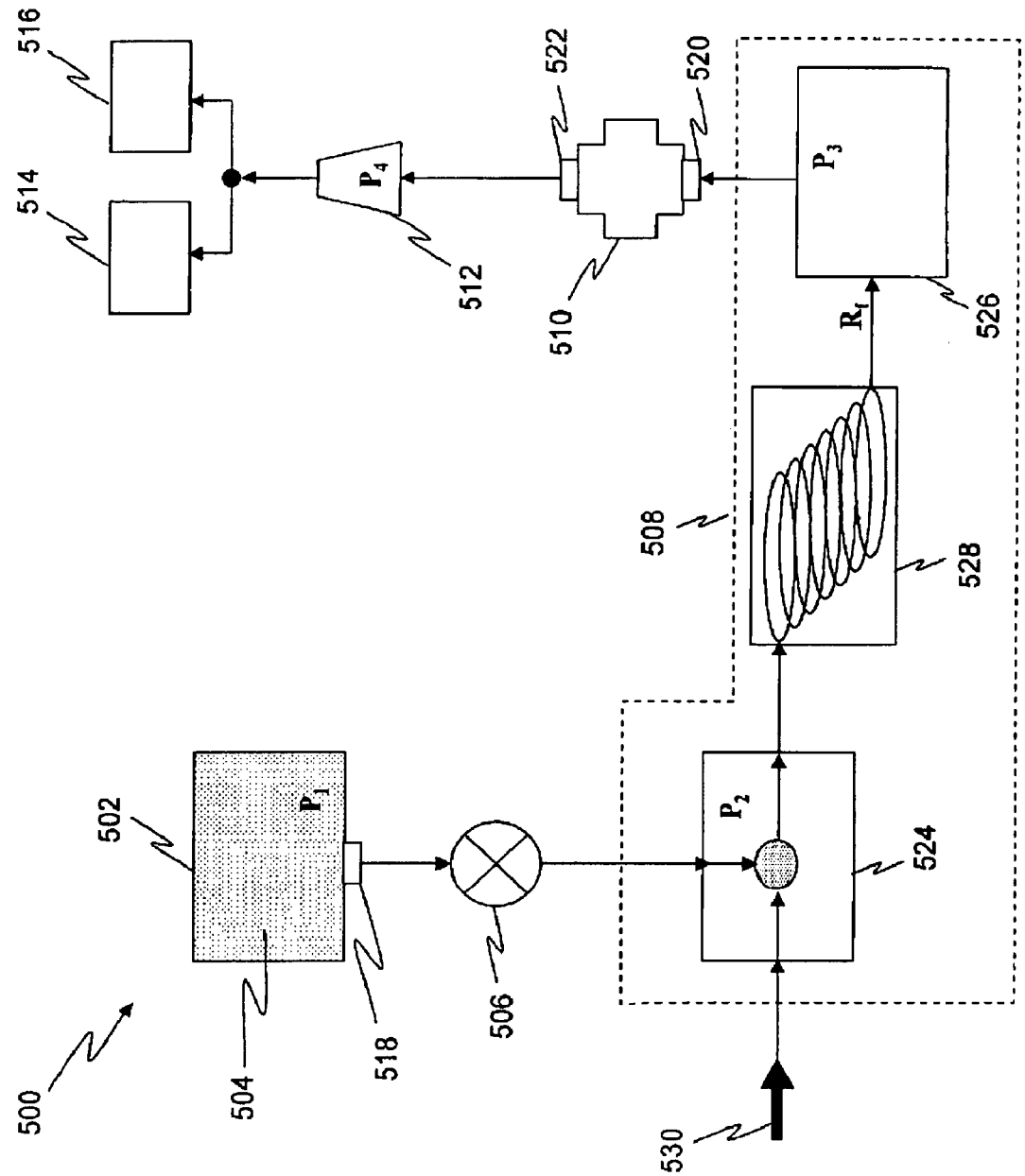
FIG. 11 is a schematic block diagram illustrating the self-contained chromatography system of FIG. 10.

Referring to FIG. 11, the gas chromatography device 508 may include an injector device 524 that is in flow communication with a detection device 526 via a chromatography column 528. As shown, the injector device 524 is configured to receive a sample substance 530 to be analyzed and the carrier gas 504 from the carrier gas reservoir outlet 518 via the pressure regulation device 506 which creates a second pressure $P_2$ within the injector device 524, wherein the first pressure $P_1$ is greater than the second pressure $P_2$ such that the pressure gradient between $P_1$ and $P_2$ allows the carrier gas 504 to controllably flow through the pressure regulation device 506 and into the injector device 524. It should be appreciated that the pressure regulation device 506 may be an optional device and may be provided to better control the flow rate through the chromatography column 528. The combined sample substance 530 and carrier gas 504 may then be introduced into the chromatography column 528 and the flow controller device 510 may be operated to generate a third pressure $P_3$ downstream of the chromatography column 528, wherein $P_2$ is larger than $P_3$ such that the pressure gradient between $P_2$ and $P_3$ allows the analyte stream to controllably flow out of the chromatography column 528, through the detection device 526 and into the flow controller device 510. The pumping device 512 may be operated to generate a fourth pressure $P_4$, wherein the fourth pressure $P_4$ is greater than the third pressure $P_3$ such that the pressure gradient between $P_4$ and $P_1$ allows the analyte stream $R_f$ to controllably flow into either the waste vessel 514 and/or the flow line 516.

Figure 12:
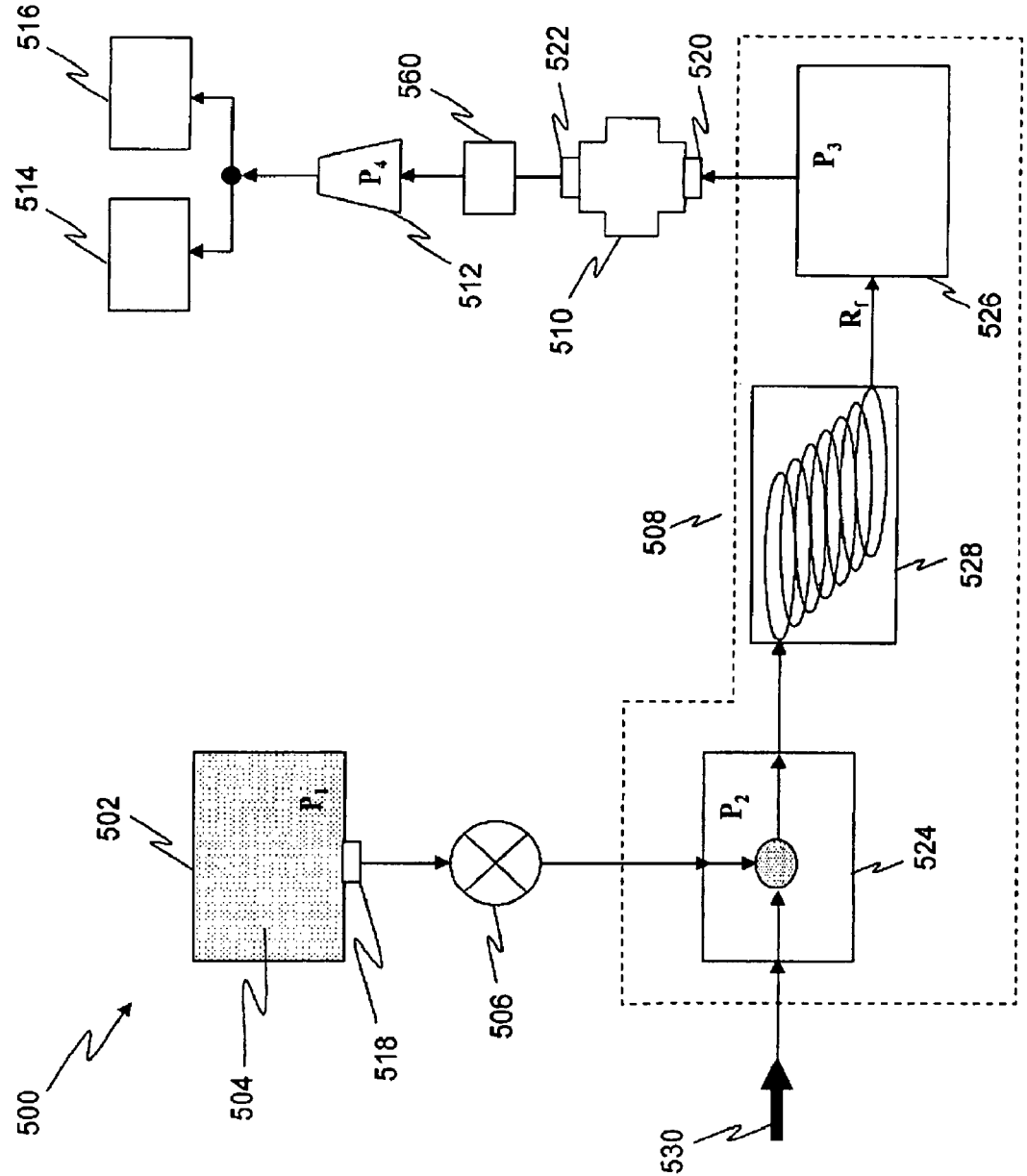
FIG. 12 is a schematic block diagram illustrating the self-contained chromatography system of FIG. 10 having an auxiliary volume.

As in the first embodiment and referring to FIG. 12, an auxiliary container 560 may be provided and disposed between the flow controller device 510 and the flow pump 512 to act as a damping device and improve the stability of the flow rate. Moreover, the flow controller device 510 and/or column flow rate may be selected in a manner responsive to the configuration of the chromatography column 528 and the detection device 526 such that even if the pressure varies downstream from the flow controller device 510, the desired flow rate through the chromatography column 528 is maintained.

It should be appreciated that the self-contained chromatography system 200 or 300 may or may not include a pumping device 212 or 312, respectively, as desired, wherein the carrier gas may be directed to the carrier gas reservoir 202 or 302 via any method and/or device suitable to the desired end purpose. For example, in the first embodiment of the self-contained chromatography system 200, hydrogen can accumulate in the reservoir 210 at pressure $P_3$ during a measurement. After completion of one or more measurements the temperature of the metal hydride may be raised to generate the pressure $P_4$. A valve may be disposed upstream to the reservoir 210 to prevent the gas from flowing back through the chromatography column 228 while the temperature and pressure of reservoir 210 are elevated. Then no pump 212 is required to generate pressure $P_4$.

As another example, in the second embodiment of the self-contained chromatography system 300, if the pumping device 312 was omitted, the carrier gas may be directed to the carrier gas reservoir 302 by operating the electrolysis cell 332 at a pressure P1.

Figure 13:
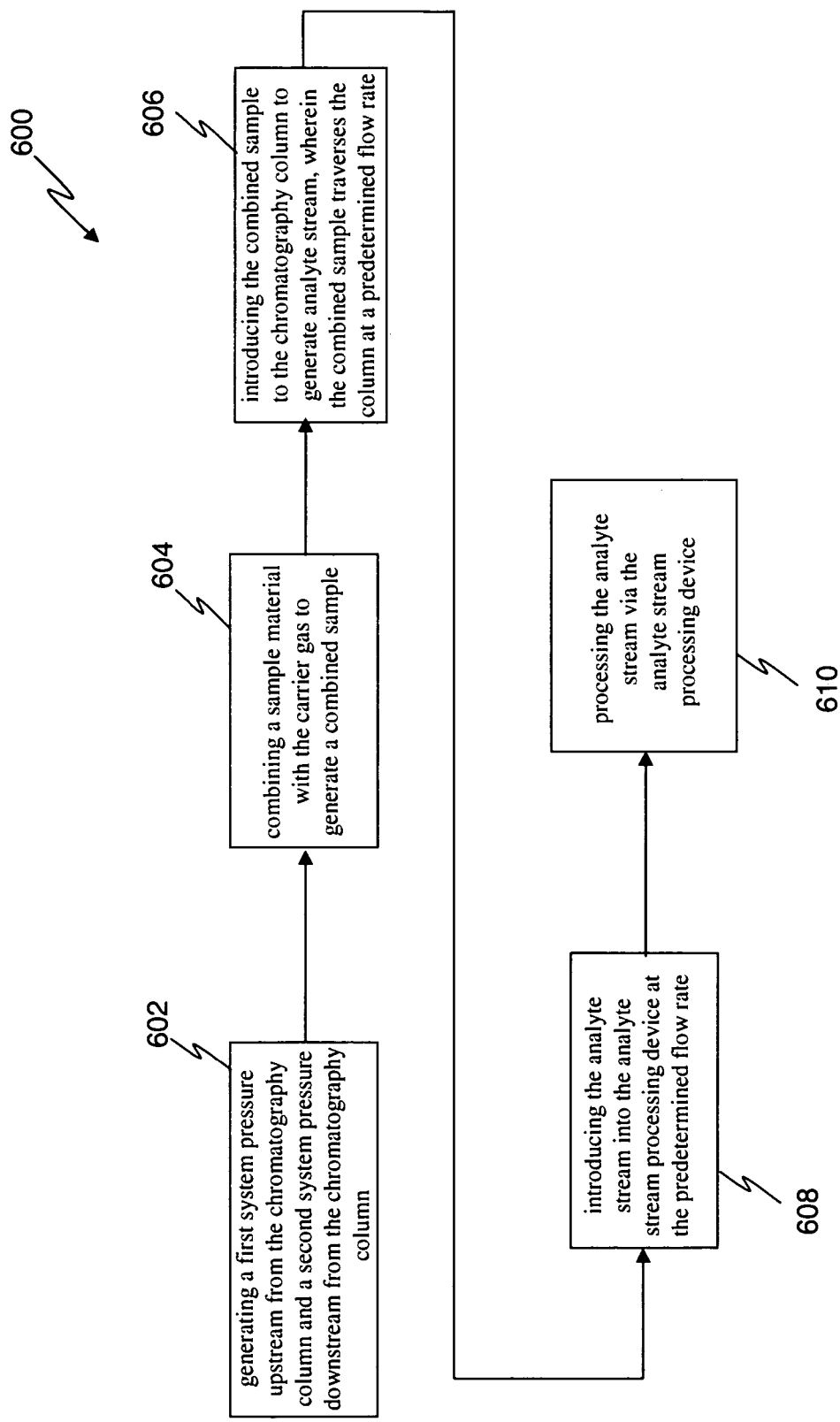
FIG. 13 is a schematic block diagram illustrating a method for implementing a self-contained chromatography system.

Referring to FIG. 13, a block diagram illustrating a method 600 for implementing a self-contained chromatography system 200, 300, 400, 500 is shown. The self-contained chromatography system 200, 300, 400, 500 includes a chromatography column 228, 326, 428, 528 a carrier gas reservoir 202, 302, 402, 502 containing a carrier gas 204, 304, 404, 504 and an analyte stream processing device 210, 310, 410, 510, wherein the carrier gas reservoir 202, 302, 402, 502 is disposed upstream from the chromatography column 228, 326, 428, 528 and wherein the analyte stream processing device 210, 310, 410, 510 is disposed downstream from the chromatography column 228, 326, 428, 528. The method 600 includes generating a first system pressure upstream from the chromatography column 228, 326, 428, 528 and a second system pressure downstream from the chromatography column 228, 326, 428, 528, as shown in operational block 602. The first system pressure and the second system pressure are such that a pressure gradient exists between the first system pressure and the second system pressure to cause the carrier gas 204, 304, 404, 504 to flow between the carrier gas reservoir 202, 302, 402, 502 and the analyte stream processing device 210, 310, 410, 510 at a controllable and predetermined flow rate.

The method 600 further includes combining a sample material 230, 328, 430, 530 with the carrier gas 204, 304, 404, 504 to generate a combined sample, as shown in operational block 604. The combined sample is then introduced into the chromatography column 228, 326, 428, 528 to generate the analyte stream, as shown in operational block 606, wherein the combined sample traverses the chromatography column 228, 326, 428, 528 at the predetermined flow rate. The analyte stream may then be introduced into the analyte stream processing device 210, 310, 410, 510, as shown in operational block 608 and processed via the analyte stream processing device 210, 310, 410, 510, as shown in operational block 610. It should be appreciated that processing may include at least one of pressurizing, purifying and/or disposing of the analyte stream.

While the invention has been described with reference to an exemplary embodiment, it should be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A method for implementing a self-contained chromatography system, wherein the self-contained chromatography system includes a chromatography column, a carrier gas reservoir containing a carrier gas and an analyte stream processing device, the carrier gas reservoir being disposed upstream from the chromatography column and the analyte stream processing device being disposed downstream from the chromatography column and including at least one pressure reservoir, wherein said pressure reservoir is at least partially comprised of a metal hydride material, the method comprising:

generating a first system pressure upstream from the chromatography column and a second system pressure downstream from the chromatography column such that a pressure gradient exists between said first system pressure and said second system pressure to cause the carrier gas to flow between the carrier gas reservoir and the analyte stream processing device at a predetermined flow rate;

combining a sample material with the carrier gas to generate a combined sample and introducing said combined sample to the chromatography column to generate the analyte stream, wherein said combined sample traverses the chromatography column at said predetermined flow rate;

introducing the analyte stream into the analyte stream processing device at said predetermined flow rate; and processing the analyte stream via the analyte stream processing device.

2. The method of claim 1, further comprising regulating said flow rate in at least one of an upstream and a downstream location relative to the chromatography column.

3. The method of claim 1, wherein at least one of said first system pressure and said second system pressure is generated by at least one pumping device.

4. The method of claim 1, wherein said processing includes generating at least one of said first system pressure and said second system pressure using at least one pressure reservoir, wherein said at least one pressure reservoir includes a metal hydride material disposed at a predetermined temperature.

5. The method of claim 4, wherein said predetermined temperature is responsive to the isobaric properties of said metal hydride material.

6. The method of claim 1, wherein said processing further includes processing said analyte stream to separate the carrier gas from said analyte stream.

7. The method of claim 1, wherein said processing further includes separating the carrier gas from said analyte stream using at least one filtration device.

8. The method of claim 1, wherein said processing further includes introducing said analyte stream into an oxidation cell, wherein said analyte stream undergoes combustion via oxidation to produce an oxidized product comprising water.

9. The method of claim 8, wherein said processing further includes separating said water from said oxidized product and introducing said water into an electrolysis cell, wherein said water undergoes electrolysis to produce hydrogen and oxygen.

10. The method of claim 9, wherein said processing further includes reintroducing said oxygen into said oxidation cell and reintroducing said hydrogen into the carrier gas reservoir.

11. The method of claim 1, wherein said processing further includes at least one of storing said analyte stream in a waste vessel and expelling said analyte stream from the self-contained chromatography system.

12. A method for implementing a self-contained chromatography system, wherein the self-contained chromatography system includes a carrier gas reservoir containing a carrier gas, wherein the carrier gas reservoir is disposed upstream from a chromatography column, the method comprising:
    combining a sample material with the carrier gas to generate a combined sample and introducing said combined sample to the chromatography column to generate an analyte stream;
    generating a first system pressure upstream from the chromatography column and a second system pressure downstream from the chromatography column such that a pressure gradient exists between said first system pressure and said second system pressure to cause said combined sample to traverse the chromatography column at a predetermined flow rate, wherein said second system pressure is generated via a pressure reservoir which is at least partially comprised of a metal hydride material; and
    processing said analyte stream to flow through the self-contained chromatography system at said predetermined flow rate.

13. A self-contained chromatography system, comprising:
    a chromatography device configured to combine a material sample to be analyzed and a carrier gas, wherein said chromatography device processes the combination of said material sample and said carrier gas to generate an analyte stream;
    a carrier gas reservoir for containing said carrier gas at a first system pressure, wherein said carrier gas reservoir is disposed upstream from said chromatography device; and
    an analyte stream processing device, wherein said analyte stream processing device includes at least one pressure reservoir for generating a second system pressure and is disposed downstream from said chromatography device to receive and process said analyte stream at said second system pressure, said first system pressure being larger than said second system pressure to cause said analyte stream to flow through said chromatography column at a desired flow rate.

14. A self-contained chromatography system, comprising:
    a chromatography device configured to combine a material sample to be analyzed and a carrier gas, wherein said chromatography device processes the combination of said material sample and said carrier gas to generate an analyte stream;
    a carrier gas reservoir for containing said carrier gas at a first system pressure, wherein said carrier gas reservoir is disposed upstream from said chromatography device; and
    an analyte stream processing device, wherein said analyte stream processing device is disposed downstream from said chromatography device to receive and process said analyte stream at a second system pressure, said first system pressure being larger than said second system pressure to cause said analyte stream to flow through said chromatography column at a desired flow rate, wherein said analyte stream processing device includes at least one pressure reservoir, wherein said pressure reservoir is at least partially comprised of a metal hydride material disposed at a predetermined temperature.

15. The self-contained chromatography system according to claim 14, wherein said carrier gas is returned to said carrier gas reservoir via a pressure differential between said carrier gas reservoir and at least one pressure reservoir.

16. The self-contained chromatography system according to claim 14, further comprising an auxiliary reservoir disposed within the chromatography system to stabilize said flow rate.

17. The self-contained chromatography system according to claim 14, further comprising at least one pressure regulation device disposed in at least one of an upstream and downstream location relative to said chromatography column.

18. The self-contained chromatography system according to claim 14, further comprising at least one pumping device, disposed in at least one of an upstream and downstream location relative to said chromatography column.

19. The self-contained chromatography system according to claim 14, wherein said analyte stream processing device includes a waste vessel.

20. The self-contained chromatography system according to claim 14, wherein said analyte stream processing device includes a flow line.

21. The self-contained chromatography system according to claim 14, wherein said analyte stream processing device includes at least one filtration device.

22. The self-contained chromatography system according to claim 14, wherein said analyte stream processing device includes an oxidation cell communicated for maintaining low downstream pressure.

23. The self-contained chromatography system according to claim 14, wherein said analyte stream processing device includes an electrolysis cell to regenerate said carrier gas.

24. The self-contained chromatography system according to claim 14, wherein said analyte stream processing device includes an oxidation cell communicated with an electrolysis cell via a first pumping device, said electrolysis cell being further communicated with said oxidation cell via an oxygen transfer tube to allow transfer of oxygen gas between said electrolysis cell and said oxidation cell.

25. The self-contained chromatography system according to claim 24, wherein said electrolysis cell is further communicated with said carrier gas reservoir via a second pumping device to allow transfer of hydrogen gas between said electrolysis cell and said carrier gas reservoir.

26. The self-contained chromatography system according to claim 24, wherein said electrolysis cell is further communicated with said carrier gas reservoir and wherein said carrier gas is returned to said carrier gas reservoir via a pressure differential between said carrier gas reservoir and said electrolysis cell.

* * * * *